United States Patent [19]

Terashima et al.

[11] Patent Number: 4,564,674
[45] Date of Patent: Jan. 14, 1986

[54] PROCESS FOR AN ANTHRACYCLINE DERIVATIVE, AND AN ANTHRACYCLINONE DERIVATIVE USEFUL FOR THE PROCESS

[75] Inventors: Shiro Terashima, Tokyo; Yoshikazu Kimura, Sagamihara; Michiyo Suzuki, Sagamihara; Teruyo Matsumoto, Sagamihara; Rumiko Abe, Sagamihara, all of Japan

[73] Assignee: Sagami Chemical Research Center, Tokyo, Japan

[21] Appl. No.: 662,833

[22] Filed: Oct. 19, 1984

[30] Foreign Application Priority Data

Oct. 31, 1983 [JP] Japan ............... 58-202733
Oct. 31, 1983 [JP] Japan ............... 58-202734

[51] Int. Cl.⁴ .................................. C07H 15/24
[52] U.S. Cl. ............................. 536/6.4; 260/365
[58] Field of Search .................. 536/6.4; 260/365

[56] References Cited

U.S. PATENT DOCUMENTS

| | | | |
|---|---|---|---|
| 4,046,878 | 9/1977 | Patelli et al. ............... | 424/180 |
| 4,161,480 | 7/1979 | Pappo et al. ................ | 260/365 |
| 4,348,388 | 9/1982 | Garland et al. .............. | 536/6.4 |

OTHER PUBLICATIONS

Acton et al., "J. Med. Chem.", vol. 17, No. 6, 1974, pp. 659–660.
El Khadem et al., "Carbohydrate Research", vol. 101, 1982, C1–C4.
El Khadem, "Academic Press", 1982, pp. 221, 265.
Monneret et al., "Academic Press", 1982, pp. 225–251.

Primary Examiner—Johnnie R. Brown
Attorney, Agent, or Firm—Oblon, Fisher, Spivak, McClelland & Maier

[57] ABSTRACT

A process for producing an anthracycline derivative represented by the general formula:

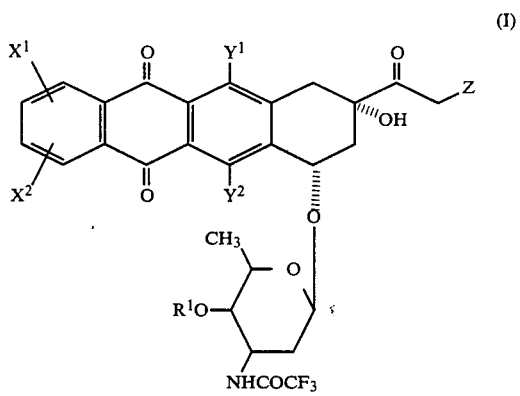

where $R^1$ is an acyl group, each of $X^1$ and $X^2$ is a hydrogen atom, a methoxy group, a hydroxyl group, a halogen atom or a lower alkyl group, each of $Y^1$ and $Y^2$ is a hydrogen atom, an alkoxy group or a hydroxyl group, and Z is a hydrogen atom or a protected hydroxyl group, which comprises reacting an anthracyclinone derivative represented by the general formula:

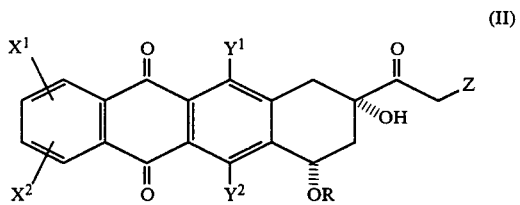

where R is a hydrogen atom or a trialkylsilyl group, and $X^1$, $X^2$, $Y^1$, $Y^2$ and Z are as defined above, with a 1-acyl-sugar derivative represented by the general formula:

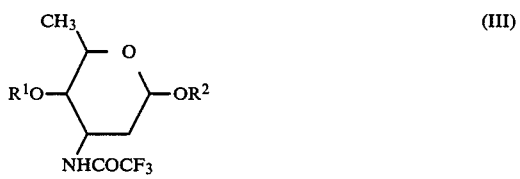

where $R^2$ is an acyl group and $R^1$ is as defined above, in the presence of a silyl sulfonic acid derivative represented by the general formula:

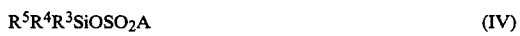

$$R^5R^4R^3SiOSO_2A \qquad (IV)$$

where each of $R^3$, $R^4$ and $R^5$ is an alkyl group and A is an alkyl group, an aryl group, a polyfluoroalkyl group or a hydrogen atom.

8 Claims, No Drawings

PROCESS FOR AN ANTHRACYCLINE DERIVATIVE, AND AN ANTHRACYCLINONE DERIVATIVE USEFUL FOR THE PROCESS

The present invention relates to a process for producing an anthracycline derivative represented by the general formula:

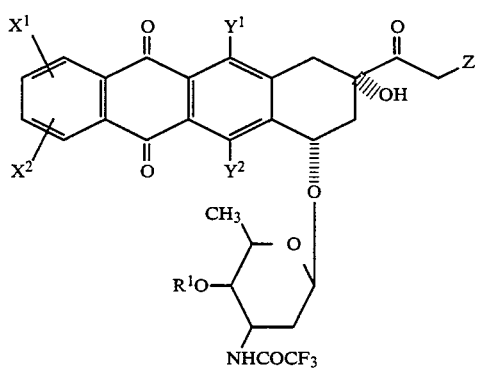

where $R^1$ is an acyl group, each of $X^1$ and $X^2$ is a hydrogen atom, a methoxy group, a hydroxyl group, a halogen atom or a lower alkyl group, each of $Y^1$ and $Y^2$ is a hydrogen atom, an alkoxy group or a hydroxyl group, and Z is a hydrogen atom or a protected hydroxyl group, and a novel hydroxy-protected anthracyclinone derivative useful for the process.

The anthracycline derivatives of the formula I obtained by the process of the present invention, can readily be converted to anthracycline antibiotics having excellent antitumour effects, such as daunomycin, 4-demethoxydaunomycin, adriamycin, 4-demethoxyadriamycin and 4-demethoxy-11-deoxyadriamycin, by removing the protective group of the hydroxyl or amino group under a mild condition.

Heretofore, there have been developed various glycoside-forming reactions for the production of the anthracycline derivatives of the formula I. Specifically, there may be mentioned (1) a method in which a reaction of an anthracyclinone derivative with a 1-halosugar derivative is conducted (a) in the presence of silver trifluoromethanesulfonate (see M. J. Broadhurst et al., J. Chem. Soc. Perkin I, 1982, 2249; Japanese Unexamined Patent Publication No. 53497/1982; F. Arcamone et al., Experientia, 34, 1255 (1978); and a Comparative Example given hereinafter) or (b) in the presence of a mixture of mercury oxide with mercury bromide or a mixture of mercury cyanide with mercury bromide (see T. H. Smith et al., J. Org. Chem., 42, 3653 (1977); F. Arcamone et al., Cancer Treat. Rep., 60, 829 (1976); Japanese Unexamined Patent Publication No. 33880/1983; Japanese Examined Patent Publication Nos. 40555/1983 and 40557/1983), (2) a method in which a reaction of an anthracyclinone derivative with glycal is conducted (a) in the presence of an acid catalyst (see Japanese Examined Patent Publication No. 40556/1983; Japanese Unexamined Patent Publication No. 149663/1975; H. Umezawa et al., J. Antibiotics, 33, 1581 (1980) or (b) in the presence of N-iodo succinimide (see D. Horton et al., "Anthracycline Antibiotics" ed. by H. S. El Khadem, Academic Press, 1982, p221), and (3) a method in which an anthracyclinone derivative is reacted with a 1-acyl-sugar derivative in the presence of p-toluenesulfonic acid or a Lewis acid (see C. Monneret et al., "Anthracycline Antibiotics", ed. by H. S. El Khadem, Academic Press, 1982, p232; H. S. El Khadem, et al., Ibid., 1982, p265; H. S. El Khadem et al., Carbohydrate Research, 101, C1 (1982); J. Boivin et al., Tetrahedron, 24, 4219 (1981); and a Comparative Example given herreinafter).

According to method (1)(a), the α-anomer is selectively obtainable. However, this method has drawbacks that it is required to use an unstable 1-halosugar derivative, and it is necessary to use expensive silver trifluoromethanesulfonate in an amount of at least the stoichiometric amount relative to the anthracyclinone derivative.

Method (1)(b) likewise requires the use of an unstable 1-halosugar derivative, and yet, in some cases, the 1-halosugar derivative is required in an amount from 3 to 9 times the amount of the anthracyclinone derivative. Further, this method has additional drawbacks that in addition to the desired α-anomer, an unnecessary β-anomer will form as a by-product, and a poisonous mercury salt is used as the glycoside-forming agent.

Method (2) has drawbacks that glycal which is obtainable by treating the 1-halosugar derivative used as a starting material in method (1), with mercury cyanide or silver carbonate, or by treating a 1-hydroxysugar derivative with p-toluenesulfonyl chloride-pyridine, is required to be used usually in an amount of from 2 to 4 times the amount of the anthracyclinone derivative, and as in the case of method (1)(b), the β-anomer is likely to form as a by-product in many cases. Further, method (2)(b) has a drawback that the glycoside-forming reaction must be followed by a deiodination reaction.

In method (3), a 1-acyl-sugar derivative is used which is more stable than the 1-halosugar derivative. However, the production ratio of the α-anomer to the β-anomer is 9:1 at best, and yet, in the case where a Lewis acid such as tin tetrachloride is used, the separation of the product after the reaction will be difficult.

Further, in any one of the methods (1) to (3), the yield of the desired anthracyline derivative is usually from 50 to 60%, i.e. an unreacted anthracyclinone derivative remains, and yet the β-anomer forms as a by-product in many cases, whereby it is required to conduct a separation operation by means of e.g. column chromatography. From the foregoing reasons, it is difficult to employ these conventional methods for the production of anthracycline derivatives on an industrial scale.

The present inventors have conducted extensive researches to overcome the difficulties of the conventional methods, and have found it possible to produce only the α-anomer with high stereo selectivity in good yield by conducting the glycoside-forming reaction by means of inexpensive reagent. The present invention has been accomplished based on this discovery. Namely, as in the case of the above-mentioned method (3), according to the present invention, it is possible to use, as the starting material, a 1-acyl-sugar derivative which is highly durable as compared with the 1-halosugar derivative thus is suitable for a storage for an extended period of time, and in the glycoside-forming reaction, the α-anomer is selectively produced with no substantial production of by-products, whereby the separation operation can readily be conducted.

Namely, the present invention provides a process for producing an anthracycline derivative represented by the general formula:

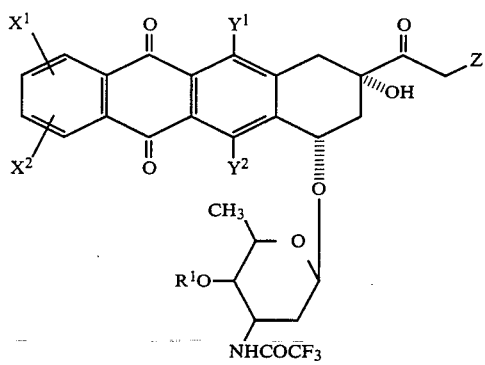

(I)

where $R^1$ is an acyl group, each of $X^1$ and $X^2$ is a hydrogen atom, a methoxy group, a hydroxyl group, a halogen atom or a lower alkyl group, each of $Y^1$ and $Y^2$ is a hydrogen atom, an alkoxy group or a hydroxyl group, and Z is a hydrogen atom or a protected hydroxyl group, which comprises reacting an anthracyclinone derivative represented by the general formula:

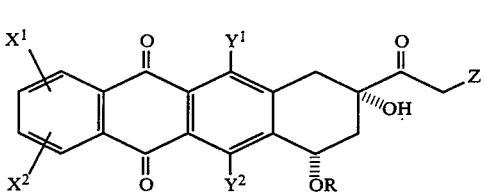

(II)

where R is a hydrogen atom or a trialkylsilyl group, and $X^1$, $X^2$, $Y^1$, $Y^2$ and Z are as defined above, with a 1-acyl-sugar derivative represented by the general formula:

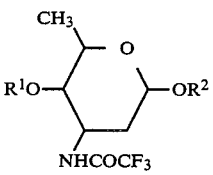

(III)

where $R^2$ is an acyl group and $R^1$ is as defined above, in the presence of a silyl sulfonic acid derivative represented by the general formula:

$$R^5R^4R^3SiOSO_2A \qquad (IV)$$

where each of $R^3$, $R^4$ and $R^5$ is an alkyl group and A is an alkyl group, an aryl group, a polyfluoroalkyl group or a hydrogen atom.

Among the anthracylinone derivatives of the formula II used as the starting material in the process of the present invention, compounds wherein R is a hydrogen atom can readily be obtained by conventional methods (see F. Arcamone, et al., Experientia, 34, 1255 (1978); H. Umezawa, et al., J. Antibiotics, 33, 1581 (1980); S. Terashima, et al., Chem. Pharm. Bull., 31, 811, 821 (1983); S. Terashima, et al., Tetrahedron Letters, 23, 4107 (1982); S. Terashima, et al., summary of the reports presented at the 43rd Symposium on Organic Synthesis, Japan, 1983, p94).

Whereas, the compounds of the formula II wherein R is a trialkylsilyl group, are new compounds. Namely, the present invention also provides a new anthracyclinone derivative represented by the general formula:

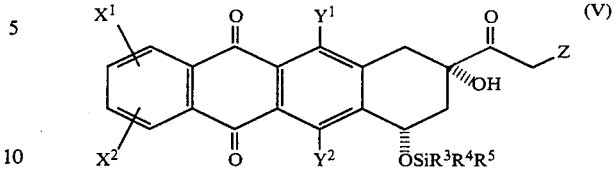

(V)

where $R^3$, $R^4$, $R^5$, $X^1$, $X^2$, $Y^1$, $Y^2$ and Z are as defined above. This new compound can readily be obtained by reacting a compound of the formula II where R is a hydrogen atom, with a ketene silyl acetal or a 1,3-diketone silylenol ether. The ketene silyl acetal is a compound obtainable by reacting $R^5R^4R^3SiCl$ to a lithium enolate formed by reacting a carboxylic acid ester with a strong base such as lithium diisopropylamide. The 1,3-diketone silyl enol ether is a compound obtainable by reacting a 1,3-diketone with $R^5R^4R^3SiCl$ in the presence of imidazole. Each of $R^3$, $R^4$ and $R^5$ is preferably a lower alkyl group such as a methyl group, an ethyl group, a propyl group or a butyl group.

Each of $X^1$ and $X^2$ in the anthracyclinone derivative of the formula II may be a hydrogen atom, a methoxy group, a hydroxyl group, a halogen atom such as a chlorine atom or a bromine atom, or a lower alkyl group such as a methyl group or an ethyl group. Each of $Y^1$ and $Y^2$ may be a hydrogen atom, an alkoxy group such as a methoxy group or an ethoxy group, or a hydroxyl group. Likewise, Z may be a hydrogen atom or a protected hydroxyl group, for instance, an acyloxy group such an acetoxy group, a t-butoxy carbonyloxy group or a benzoyloxy group; an alkoxy group such as a methoxy group, a benzyloxy group, a tetrahydropyranyloxy group, a 2-methoxyethoxy group or a (2-methoxyethoxy)methoxy group; or a trialkyl silyloxy group such as a trimethyl silyloxy group or a dimethyl-t-butylsilyloxy group. The protected hydroxyl group may further represent, together with the adjacent carbonyl group, a protective group of the formula:

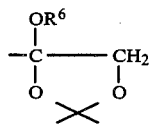

where $R^6$ is a lower alkyl group, or, together further with the 9-hydroxyl group, a protective group of the formula:

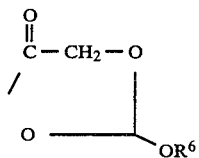

where $R^6$ is a lower alkyl group.

The 1-acyl-sugar derivative of the formula III is a compound which is readily obtainable from the corresponding aminosugar. Each of $R^1$ and $R^2$ is an acyl group such as a p-nitrobenzoyl group, a trifluoroacetyl group, an acetyl group or a benzoyl group. The 1-acyl-sugar derivative is usually employed in an amount of from 1.1 to 1.5 equivalents relative to 1 equivalent of the anthracyclinone derivative of the formula II.

Specific examples of the 1-acyl-sugar derivative of the formula III include 2,3,6-trideoxy-1,4-di-O-acyl-3-trifluoroacetamido-α-L-lyxohexopyranose, 2,3,6-trideoxy-1,4-di-O-acyl-3-trifluoroacetamido-α-L-arabino-hexopyranose, 2,3,6-trideoxy-1,4-di-O-acyl-3-trifluoroacetamido-α-L-ribo-hexopyranose, 2,3,6-trideoxy-1,4-di-O-acyl-3-trifluoroacetamido-α-D-lyxohexopyranose, 2,3,6-trideoxy-1,4-di-O-acyl-3-trifluoroacetamido-α-D-arabino-hexopyranose, and 2,3,6-trideoxy-1,4-di-O-acyl-3-trifluoroacetamido-α-D-ribo-hexopyranose.

The reaction of the process of the present invention is conducted in the presence of a silyl sulfonic acid derivative of the formula IV. As the silyl sulfonic acid derivative, there may be employed trimethylsilyl trifluoromethanesulfonate, trimethylsilyl difluoromethanesulfonate, trimethylsilyl chlorodifluoromethanesulfonate, trimethylsilyl 1,1,2,2-tetrafluoroethanesulfonate, triethylsilyl trifluoromethanesulfonate, dimethylisopropylsilyl trifluoromethanesulfonate, t-butyldimethylsilyl trifluoromethanesulfonate, trimethylsilyl perfluorobutanesulfonate, trimethylsilyl perfluorooctanesulfonate, trimethylsilyl methanesulfonate, trimethylsilyl ethanesulfonate, trimethylsilyl benzenesulfonate, trimethylsilyl p-bromobenzenesulfonate or trimethylsilyl p-toluenesulfonate. The silyl sulfonic acid derivative of the formula IV is used usually in an amount of from 0.1 to 4 equivalents relative to 1 equivalent of the anthracyclinone of the formula II where R is a hydrogen atom, or from 0.05 to 0.3 equivalent relative to 1 equivalent of the anthracyclinone of the formula II where R is a trialkylsilyl group.

The reaction of the process of the present invention is preferably conducted in a solvent. For instance, there may be employed a solvent mixture comprising a halogen-type solvent such as methylene chloride or 1,2-dichloroethane, and an ether-type solvent such as diethyl ether or demethoxyethane.

The reaction proceeds smoothly usually at a temperature of from $-20°$ to $20°$ C.

The novel anthracyclinone derivative according to the present invention is preferably represented by the general formula:

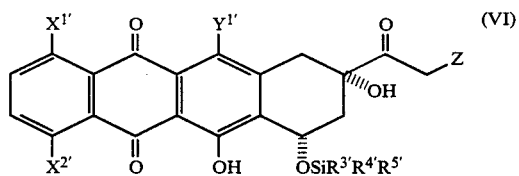

where each of $R^{3'}$, $R^{4'}$ and $R^{5'}$ is a lower alkyl group, each of $X^{1'}$ and $X^{2'}$ is a hydrogen atom, a hydroxyl group or a methoxy group, $Y^{1'}$ is a hydrogen atom or a hydroxyl group, and Z is a hydrogen atom or a protected hydroxyl group. The preferred compound of the formula VI may be prepared by reacting a compound of the general formula:

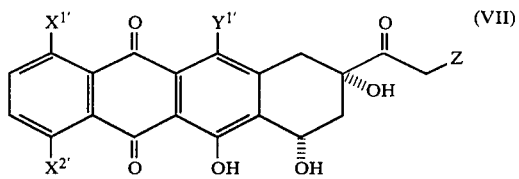

where $X^{1'}$, $X^{2'}$, $Y^{1'}$ and Z are as defined above, with a ketene silyl acetal represented by the general formula:

where $R^{3'}$, $R^{4'}$, and $R^{5'}$ are as defined above, and each of $R^7$ and $R^8$ is a lower alkyl group, or a 1,3-diketone silyl enol ether represented by the general formula:

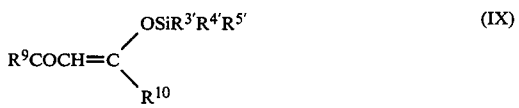

where $R^{3'}$, $R^{4'}$ and $R^{5'}$ are as defined above, and each of $R^9$ and $R^{10}$ is a lower alkyl group.

As mentioned above with respect to the compounds of the formula II where R is a hydrogen atom, the compound of the formula VII may readily be obtained by the conventional methods.

The ketene silyl acetal represented by the general formula VIII is commercially available or may readily be prepared by a conventional method (see Y. Kita et al., Tetrahedron Letters, 1979, 4311). Each of $R^{3'}$, $R^{4'}$, $R^{5'}$, $R^7$ and $R^8$ is a lower alkyl group such as a methyl group, an ethyl group, a propyl group or a butyl group.

The 1,3-diketone silyl enol ether of the formula IX is a compound obtainable by reacting the 1,3-diketone with $R^{5'}R^{4'}R^{3'}SiCl$ in the presence of imidazole. Each of $R^9$ and $R^{10}$ is a lower alkyl group such as a methyl group, an ethyl group, a propyl group or a butyl group.

The reaction is preferably conducted in a solvent, for example, a halogen-type solvent such as methylene chloride or dichloroethane; an ether-type solvent such as diethyl ether, THF or demethoxyethane; or an aromatic solvent such as benzene, toluene or xylene. The reaction usually proceeds smoothly at a temperature of from $-20°$ to $20°$ C.

Now, the present invention will be described in detail with reference to Examples. However, it should be understood that the present invention is by no means restricted by these specific Examples.

REFERENCE EXAMPLE 1

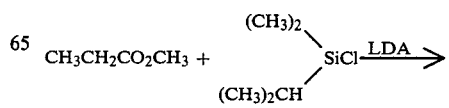

-continued

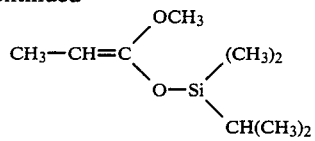

One g of diisopropyl amine was dissolved in 7.5 ml of THF at 0° C., and 7 ml of a 1.6M BuLi hexane solution was dropwise added. The mixture was stirred for 15 minutes at 0° C. The reaction solution was cooled to −78° C., and then 0.88 g (10 mmol) of methyl propionate was added. Thirty minutes later, 1.64 g (12 mmol) of dimethyl isopropyl silyl chloride was added thereto, and the mixture was stirred for 30 minutes. To the reaction solution, 1.9 ml of methyl iodide and 5 ml of pentane were added at −78° C., and then the reaction mixture was stirred at 0° C. for 30 minutes by means of ice bath. Then, the reaction mixture was left to stand overnight in a refrigerator. The reaction mixture was subjected to filtration, and the filtrate was distilled under reduced pressure, whereby 1.24 g (66%) of crude methylketene methyl dimethylisopropylsilyl acetal was obtained. NMR(CCl$_4$)δ(ppm): 0.12(6H, s, (CH$_3$)$_2$Si), 0.96(6H, s, CH(CH$_3$)$_2$), 0.99(1H, s, CH(CH$_3$)$_2$), 1.40(3H, d, J=6 Hz, =CHCH$_3$), 3.45(3H, s, OCH$_3$), 3.57(1H, q, J=6 Hz, CH$_3$CH=).

This product was used for the reaction of Example 2 without purification.

EXAMPLE 1

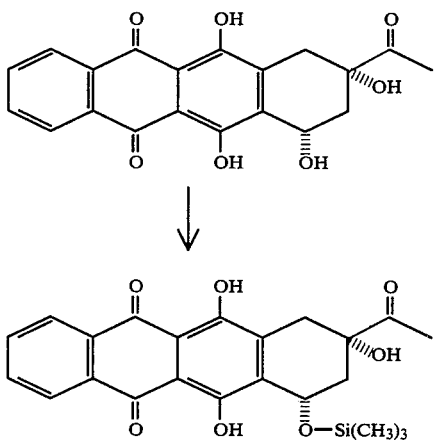

Ninety mg (0.24 mmol) of 4-demethoxydaunomycinone was dissolved in anhydrous methylene chloride, and 220 mg (1.38 mmol) of methylketene methyl trimethylsilyl acetal [bp: 45°–47° C./23 mmHg (lit., bp: 46.3°–46.5° C./23 mmHg) synthesized in accordance with the method disclosed by Y. Kita et al., Tetrahedron Lett., 1979, 4311] was added thereto. The mixture was refluxed for 3 hours in an argon stream. The reaction solution was cooled, and the solvent and unreacted methylketene methyl trimethylsilyl acetal were distilled off under reduced pressure. The residue was purified by silica gel column chromatography (benzene/ethyl acetate=4), whereby 92.3 mg (86%) of 7-trimethylsilyl-4-demethoxydaunomycinone was obtained. The 7-trimethylsilyl-4-demethoxydaunomycinone was recrystallized from hexane/benzene=4 to obtain a sample for analysis.

Mp: 164°–165° C. [α]$_D^{20}$+210°(c 0.10 dioxane).

NMR(CDCl$_3$)δ(ppm): 0.30(9H, s, (CH$_3$)$_3$Si), 1.88–2.20(2H, m, 2H$_8$), 2.45(3H, s, COCH$_3$), 2.95(1H, d, J=18 Hz, H$_{10ax}$), 3.30(1H, d, J=18 Hz, H$_{10eq}$), 5.43(2H, brs, H$_7$+9—OH), 7.73–7.95(2H, m, ArH), 8.22–8.42(2H, m, ArH), 13.33(1H, 2, ArOH), 13.60(1H, s, ArOH).

Elemental analysis: As C$_{23}$H$_{24}$O$_7$Si. Calculated value: C: 62.70, H: 5.49%. Measured value: C: 62.63, H: 5.49%.

EXAMPLE 2

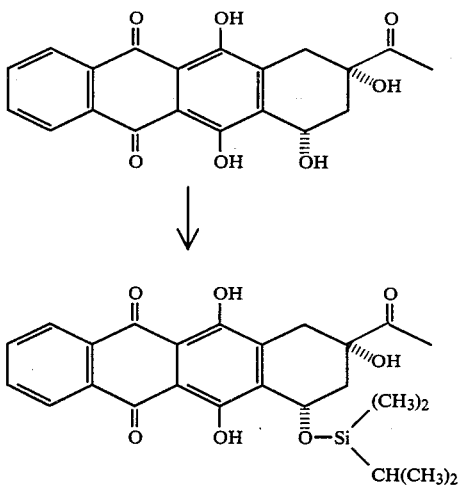

In 2 ml of anhydrous methylene chloride, 10.2 mg (0.028 mmol) of 4-demethoxydaunomycinone was dissolved, and 36.0 mg (0.192 mmol) of methylketene methyl dimethylisopropylsilyl acetal (synthesized in Reference Example 1) was added thereto. The mixture was refluxed for 2 hours. The reaction solution was treated in the same manner as in Example 1, and the residue was purified by silica gel column chromatography (benzene/ethyl acetate=50), whereby 9.0 mg (69%) of 7-dimethylisopropylsilyl-4-demethoxydaunomycinone was obtained.

NMR(CDCl$_3$)δ(ppm): 0.29(6H, s, (CH$_3$)$_3$Si), 0.96(6H, s, CH(CH$_3$)$_2$), 0.99(1H, s, CH(CH$_3$)$_2$), 1.88–2.20(2H, m, 2H$_8$), 2.43(3H, s, COCH$_3$), 2.95(1H, d, J=18 Hz, H$_{10ax}$), 3.30(1H, d, J=18 Hz, H$_{10eq}$), 5.44(2H, brs, H$_7$+9—OH), 7.73–7.95(2H, m, ArH), 8.22–8.42(2H, m, ArH), 13.30(1H, s, ArOH), 13.60(1H, s, ArOH).

EXAMPLE 3

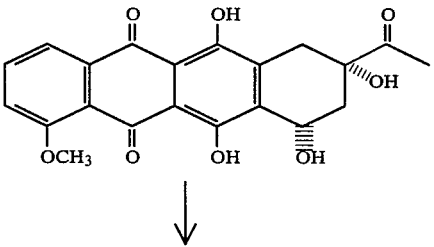

-continued

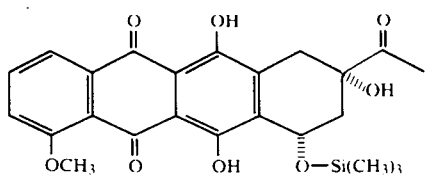

In 30 ml of anhydrous methylene chloride, 46.0 mg (0.012 mmol) of daunomycinone was dissolved, and 105 mg (0.66 mmol) of methylketene methyl trimethylsilyl acetal was added thereto. The mixture was refluxed for 3 hours in an argon stream. The volatile fraction was distilled off from the reaction solution under vacuum, and the residue was purified by silica gel column chromatography, whereby 7-trimethylsilyl daunomycinone was obtained. The yield was 47.7 mg (84%).

NMR(CDCl$_3$)δ(ppm): 0.30(9H, s, (CH$_3$)$_3$Si), 1.89–2.20(2H, m, H$_8$) 2.45(3H, s, COCH$_3$), 2.97(1H, d, J=18 Hz, H$_{10ax}$), 3.32(1H, d, J=18 Hz, H$_{10eq}$), 4.02(1H, s, OCH$_3$), 5.44 (2H, brs, H$_7$+9−OH), 7.25–8.03(3H, m, ArH), 12.85(1H, s, ArOH), 13.54(1H, s, ArOH).

EXAMPLE 4

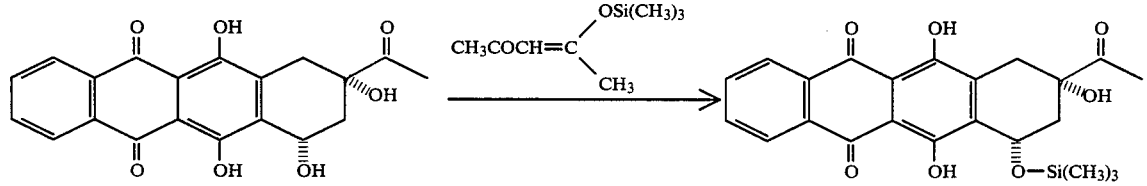

In 8 ml of anhydrous methylene chloride, 40.0 mg (0.109 mmol) of 4-demethoxydaunomycinone was dissolved, and 140 mg (0.81 mmol) of 2,4-pentanedione trimethyl silyl enol ether (synthesized by the process of T. Veysoglu et al., Tetrahedron Lett. 22, 1303 (1981)) was added thereto. The mixture was refluxed for 2 hours. The volatile fraction was distilled off from the reaction solution under vacuum, and the residue was subjected to silica gel short column (developed by benzene, followed by benzene/ethyl acetate=4), whereby 7-trimethylsilyl-4-demethoxydaunomycinone was obtained. Yield was 43.6 mg (92%).

The NMR spectrum was the same as the one obtained in Example 1.

EXAMPLE 5

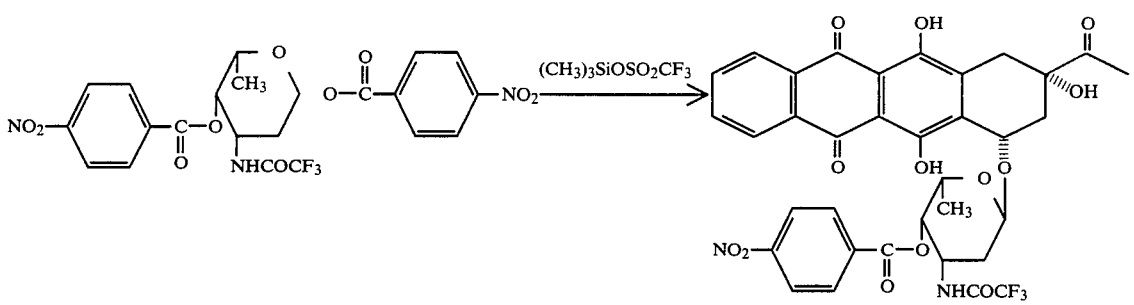

0.06 ml (0.31 mmol) of trimethylsilyl trifluoromethane sulfonate was added at −40° C. to a mixture comprising 82.8 mg (0.15 mmol) of 2,3,6-trideoxy-1,4-di-O-p-nitrobenzoyl-3-trifluoroacetamido-α-L-lyxohexopyranose [mp: 202°–203° C. (Lit., mp: 203°–204° C.), synthesized by the method disclosed in J. Org. Chem., 42, 3653 (1977)], 400 mg of molecular sieve 4A, 4 ml of anhydrous methylene chloride and 4 ml of anhydrous ether, and the mixture was stirred for 0.5 hour at a temperature of from −3° to −5° C. The reaction solution was cooled to a temperature of from −15° to −20° C., and then 14 ml of an anhydrous methylene chloride solution containing 42.0 mg (0.11 mmol) of 4-demethoxydaunomycinone was dropwise added over a period of 10 minutes. Then, the stirring was continued at the same temperature for 20 minutes. The reaction solution was poured into a mixture comprising 50 ml of a saturated sodium hydrogen carbonate solution and 50 ml of ethyl acetate and vigorously stirred at 0° C., to stop the reaction. The organic layer was separated, washed with a saturated sodium chloride solution, dried over anhydrous magnesium sulfate and then subjected to distillation for the removal of the solvent. The residual TLC showed that 4-demethoxydaunomycinone disappeared completely. The product was subjected to silica gel short column (benzene/ethyl acetate=4), whereby 80.0 mg (yield: 98%) of 4′-O-p-nitrobenzoyl-3′-N-trifluoroacetyl-4-demethoxy daunomycin was obtained as orange colored crystals.

Mp: 165°–170° C. [α]$_D^{20}$−88.6° (c=0.10, dioxane) (lit, mp: 171°–175° C., [α]$_D^{20}$−89.8° (c=0.1, dioxane); M. J. Broadhurst et al., J. Chem, Soc., Perkin I, 1982, 2249).

NMR(CDCl₃)δ(ppm): 1.25(3H, d, J=6 Hz), 6'-CH₃), 1.98-2.38 (4H, m, 2H₂'+2H₈), 2.45(3H, s, COCH₃), 3.00(1H, d, J=19 Hz, H₁₀ₐₓ), 3.36(1H, d, J=19 Hz, H₁₀ₑq), 4.22(1H, s, 9-OH), 4.34-4.66(2H, m, H₃'+H₅') 5.36(1H, brs, H₇), 5.51(1H, m, H₄'), 5.70(1H, brs, W_H=6 Hz, H₁'), 6.24(1H, brd, J=7 Hz, NH), 7.76-7.94(2H, m, ArH), 8.20-8.48(6H, m, ArH), 13.35(1H, s, ArOH), 13.68(1H, s, ArOH).

REFERENCE EXAMPLE 2

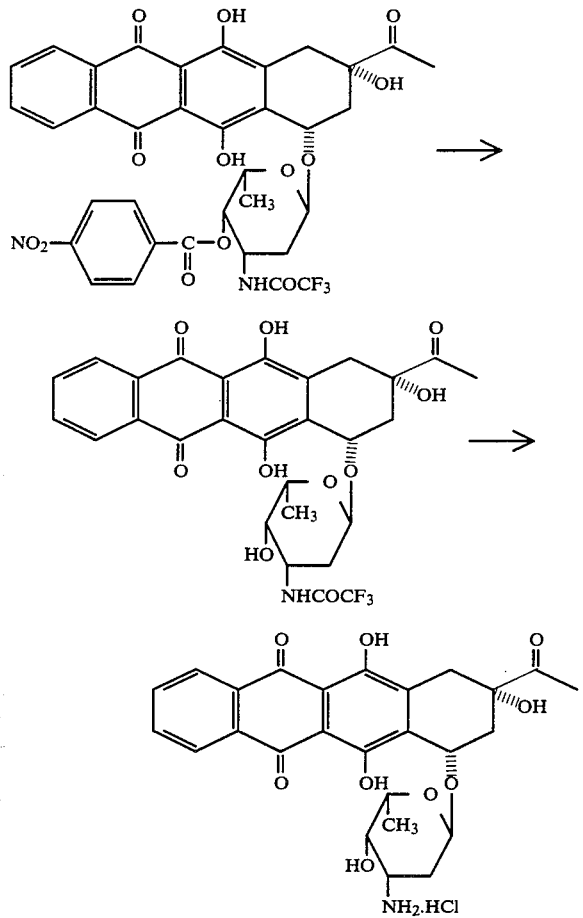

In 1 ml of methylene chloride and 100 ml of methanol, 74.3 mg (0.10 mmol) of 4'-O-p-nitrobenzoyl-3'-N-trifluoroacetyl-4-demethoxydaunomycin was dissolved, and 2 ml of a 0.1N aqueous sodium hydroxide solution was added at 0° C. The mixture was stirred for 20 minutes. The reaction solution was neutralized with glacial acetic acid until the solution turned orange. Then, 100 ml of water was added thereto, and the mixture was extracted with ethyl acetate (2×50 ml). The extracted solution was washed with a saturated sodium chloride solution (30 ml) and dried over anhydrous magnesium sulfate, and then the solvent was distilled off under reduced pressure. The residue was purified by silica gel column chromatography (chloroform/acetone=15), whereby 55.5 mg (yield: 98%) of 3'-N-trifluoroacetyl-4-demethoxydaunomycin was obtained.

Mp: 150°-154° C. $[\alpha]_D^{20}$+190° (c=0.10, dioxane) (lit, mp: 155°-156° C., $[\alpha]_D^{20}$+190° (c=0.1, dioxane): M. J. Broadhurst, et al., J. Chem, Soc. Perkin I, 1982, 2249).

NMR(CDCl₃)δ(ppm): 1.34(3H, d, J=7 Hz, 6'-CH₃), 1.80-2.38 (4H, m, 2H₈+2H₂'), 2.43(3H, s, COCH₃), 2.99(1H, d, J=19 Hz, H₁₀ₐₓ), 3.34(1H, dd, J=19, 1.5 Hz, H₁₀ₑq), 3.62-3.78(1H, m, H₄'), 4.32(1H, s, 9-OH), 4.10-4.42 (2H, m, H₃'+H₅'), 5.30(1H, dd, J=4.2 Hz, H₇), 5.54 (1H, brd, J=3 Hz, H₁'), 6.67(1H, brd, J=8 Hz, NH), 7.81-7.93(2H, m, ArH), 8.35-8.47(2H, m, ArH), 13.38(1H, s, ArOH), 13.66(1H, s, ArOH).

IR(KBr): 3350(NH), 3475(OH), 1720(CO)cm⁻¹.

Seventy seven mg (0.14 mmol) of 3'-N-trifluoroacetyl-4-demethoxydaunomycin was stirred for 30 minutes in 15 ml of a 0.1N aqueous sodium hydroxide solution in an argon stream. The reaction solution was adjusted to pH 8 with 5N HCl, and was extracted with chloroform (5×30 ml). The extracted solution was washed with 50 ml of water and dried over anhydrous magnesium sulfate, and then the solvent was distilled off. The residue was dissolved in a small amount of methanol-chloroform (1:10), and then 0.6 ml of a 0.25N HCl methanol solution was added. Then, the mixture was diluted with 20 ml of ether, whereby crystals of 4-demethoxydaunomycin hydrochloride precipitated. The yield was 45.2 mg (65%).

Mp: 184°-187° C. (decomposition) (lit, 183°-185° C.: F. Arcamone, et al., Cancer Treatment Rep. 60, 829 (1976)). $[\alpha]_D^{20}$+188° (c=0.10,CH₃OH) (lit, +187° (c=0.1, CH₃OH): M. J. Broadhurst, et al., J, Chem. Soc. Perkin I, 1982, 2249).

NMR(d₆-DMSO)δ(ppm): 1.15(3H, d, J=6 Hz, 6'-CH₃), 1.60-2.22(4H₁, m, 2H₂'+2H₈), 2.30(3H, s, COCH₃), 2.97(2H, brs, 2H₁₀), 3.50-3.73(1H, brs, H₄'), 4.22(1H, brd, J=6 Hz, H₅'), 4.95(1H, brs, H₇), 5.33(1H, brs, W_H=6 Hz, H₁'), 5.36-5.62(2H, m, 9-OH+4'-OH), 7.85-8.12(2H, brs, ArH), 8.18-8.34(2H, brs, ArH).

EXAMPLE 6

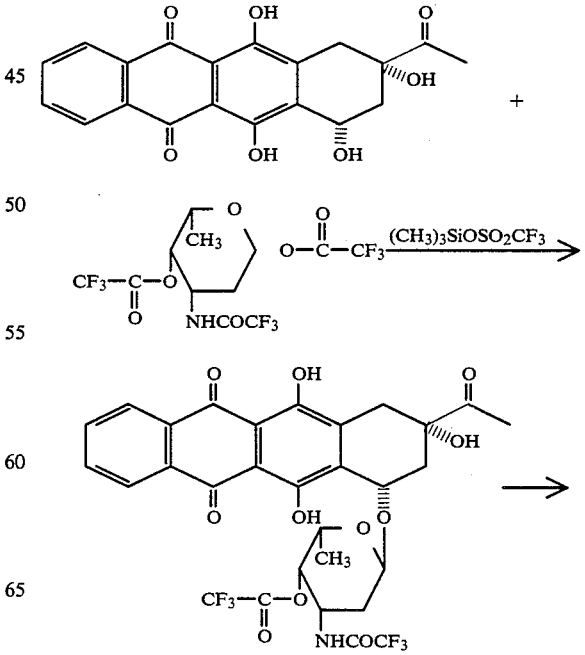

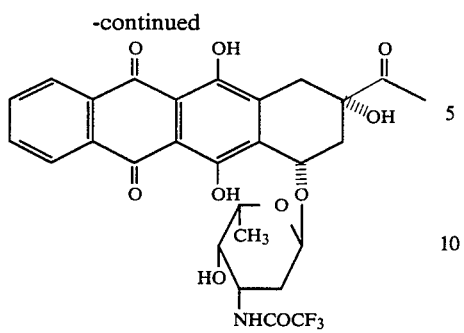

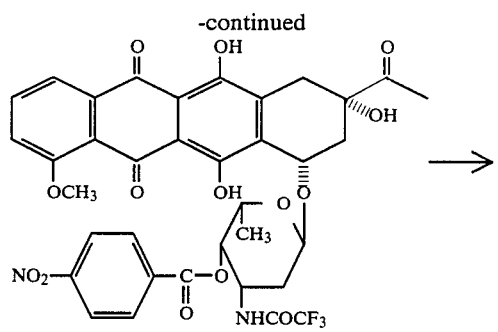

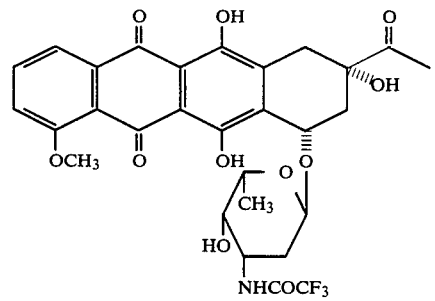

0.06 ml (0.31 mmol) of trimethylsilyl trifluoromethanesulfonate was added at −40° C. to a mixture comprising 61.0 mg (0.15 mmol) of 2,3,6-trideoxy-1,4-di-O-trifluoroacetyl-3-trifluoroacetamido-α-L-lyxohexopyranose [mp: 133°–135° C. (lit., 132°–134° C.), synthesized by the method of Japanese Examined Patent Publication No. 33880/1983], 400 mg of molecular sieve 4A, 4 ml of anhydrous methylene chloride and 4 ml of anhydrous ether, and the mixture was stirred for 0.5 hour at 40° C. To the reaction solution, 14 ml of a methylene chloride solution containing 41.5 mg (0.11 mmol) of 4-demethoxydaunomycinone, was dropwise added over a period of 10 minutes, and the mixture was stirred for further 20 minutes. Then, the temperature of the reaction solution was raised to −2° C., and the solution was stirred for 2 hours at the same temperature. Then, the reaction mixture was treated in the same manner as in Example 5, whereby 3′,4′-N,O-bistrifluoroacetyl-4-demethoxydaunomycin was obtained. The 3′,4′-N,O-bistrifluoroacetyl-4-demethoxydaunomycin was converted to N-trifluoroacetyl-4-demethoxydaunomycin to confirm its structure. Namely, the 3′,4′-N,O-bistrifluoroacetyl-4-demethoxydaunomycin was dissolved in 30 ml of methanol, hydrolyzed at 0° C. with 2 ml of 0.1N NaOH (for 20 minutes), and then neutralized with glacial acetic acid, followed by extraction, washing with water and drying. The product is then purified by silica gel column chromatography (chloroform/acetone=15), whereby 40.0 mg (yield: 61%) of N-trifluoroacetyl-4-demethoxydaunomycin was obtained. The NMR and IR spectra were the same as obtained in Reference Example 2.

EXAMPLE 7

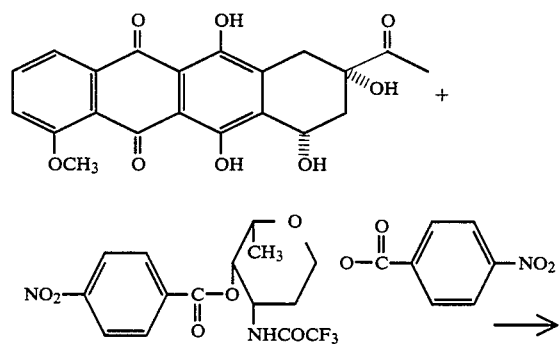

0.03 ml of trimethylsilyl trifluoromethanesulfonate was added at −40° C. to a mixture comprising 40.0 mg (0.074 mmol) of 2,3,6-trideoxy-1,4-di-O-p-nitrobenzoyl-3-trifluoroacetamido-α-L-lyxohexopyranose, 200 mg of molecular sieve 4A, 2 ml of anhydrous methylene chloride and 2 ml of anhydrous ether, and the mixture was stirred at −3° C. for 0.5 hour. Then, 6 ml of a methylene chloride solution containing 21.3 mg (0.056 mmol) of daunomycinone was added thereto at −15° C., and the mixture was reacted for 30 minutes. Then, the reaction mixture was treated in the same manner as in Example 5, whereby 4′-O-p-nitrobenzoyl-3′-N-trifluoroacetyl-daunomycin was obtained. Yield was 41.0 mg (95%). The 4′-O-p-nitrobenzoyl-3′-N-trifluoroacetyl-daunomycin was hydrolyzed in methanol with 0.1N NaOH and converted to N-trifluoroacetyldaunomycin to ascertain its structure.

Mp: 170°–172° C., $[\alpha]_D^{23} = +214°$ (c=0.10, CHCl$_3$) (lit., mp: 170°–171° C., $[\alpha]_D^{23} = +235°$ (c=0.1, CHCl$_3$); see Japanese Examined Patent Publication No. 40556/1973).

NMR(CDCl$_3$)δ(ppm): 1.33(3H, d, J=7 Hz, CH$_3$), 1.95–2.35(4H, m, 2H$_8$+2H$_{2'}$), 2.41(1H, s, COCH$_3$), 2.98(1H, d, J=19 Hz, H$_{10ax}$), 3.34(1H, dd, J=19, 1.5 Hz, H$_{10eq}$), 3.62–3.77 (1H, m, H$_{4'}$), 4.02(1H, s, OCH$_3$), 4.33(1H, s, 9-OH), 4.11–4.42(2H, m, H$_{3'}$+H$_{5'}$), 5.15(1H, brs, H$_7$), 5.40 (1H, brd, J=3 Hz, H$_{1'}$), 6.70(1H, brd, J=8 Hz), NH), 7.24–8.00(3H, m, ArH), 12.90(1H, s, ArOH), 13.65(1H, s, ArOH).

EXAMPLE 8

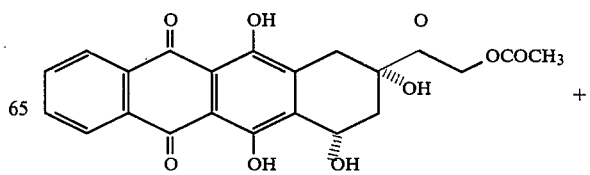

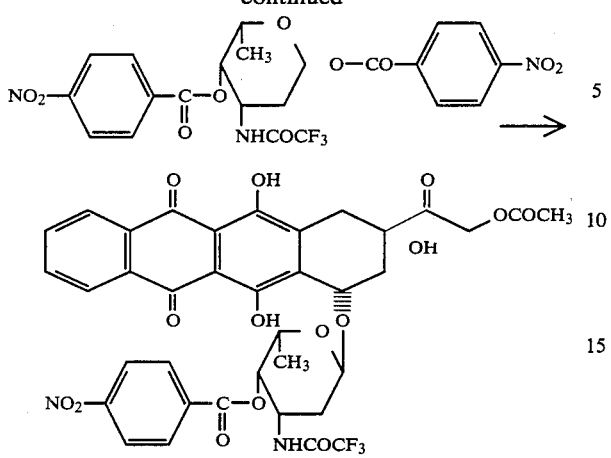

0.04 ml of trimethyl silyl trifluoromethane sulfonate was added at −40° C. to a mixture comprising 35.5 mg (0.066 mmol) of 2,3,6-trideoxy-1,4-di-O-p-nitrobenzoyl-3-trifluoroacetamido-α-L-lyxohexopyranose, 2 ml of methylene chloride and 2 ml of ether, and the mixture was stirred at a temperature of from 0° to −3° C. for 30 minutes. Then, 8 ml of a methylene chloride solution containing 22.0 mg (0.052 mmol) of 14-acetoxy-4-demethoxydaunomycinone (synthesized in Reference Example 3) was dropwise added thereto at −15° C., and the mixture was stirred for 1 hour. The reaction mixture was treated in the same manner as in Example 5, whereby 38.1 mg (yield: 92%) of 4'-O-p-nitrobenzoyl-3'-N-trifluoroacetyl-14-acetoxy-4-demethoxydaunomycin was obtained.

Mp: 168°–172° C.

NMR(CDCl$_3$)δ(ppm): 1.30(3H, d, J=6 Hz, 6'-CH$_3$), 2.00–2.68 (4H, m, 2H$_{2'}$+2H$_8$), 2.22(3H, s, COCH$_3$), 3.10(1H, d, J=19 Hz, H$_{10ax}$), 3.44(1H, dd, J=19, 1.5 Hz, H$_{10eq}$), 4.39 (1H, s, 9-OH), 4.35–4.60(2H, m, H$_{3'}$+H$_{5'}$), 5.10(1H, d, J=19 Hz, H$_{14}$), 5.40(1H, brs, H$_7$), 5.44(1H, d, J=19 Hz, H$_{14}$), 5.54(1H, brs, H$_{4'}$), 5.74(1H, brs, W$_H$=6 Hz, H$_{1'}$), 6.31(1H, brs, J=8 Hz, NH), 7.80–7.98(2H, m, ArH), 8.20–8.50(6H, m, ArH), 13.33(1H, s, ArOH), 13.69(1H, s, ArOH).

IR(KBr): 3500(NH), 3350(OH), 1730(CO)cm$^{-1}$.

Elemental analysis: As C$_{37}$H$_{31}$F$_3$N$_2$O$_{15}$·2H$_2$O. Calculated value: C: 53.11, H: 4.19, N: 3.35%. Measured value: C: 53.06, H: 3.96, N: 3.56%.

REFERENCE EXAMPLE 3

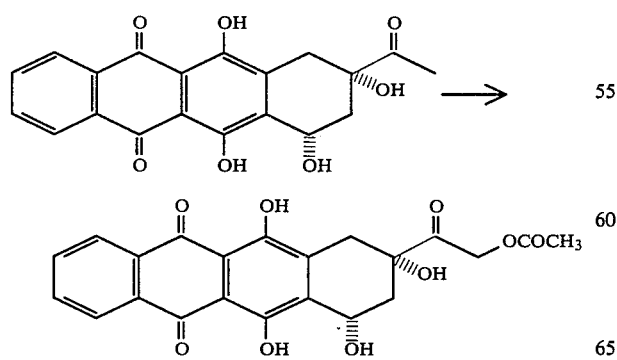

In 7.5 ml of THF, 74.0 mg (0.20 mmol) of 4-demethoxydaunomycinone was dissolved, and 74.0 mg (0.23 mmol) of pyridinium bromide perbromide was added thereto. The mixture was stirred for 2.5 hours. To the reaction solution, 7.5 ml of acetone was added, and the mixture was stirred for 15 minutes. Then, 225 mg (2.30 mmol) of anhydrous potassium acetate was added thereto, and the mixture was stirred for 1.5 hours. The solvent was distilled off under reduced pressure, and after an addition of 25 ml of water, the residue was extracted with methylene chloride (3×20 ml). The extracted solution was washed successively with water and a saturated aqueous sodium chloride solution, and then dried over anhydrous magnesium sulfate. The solvent was distilled off, and the residue was purified by silica gel colomn chromatography (benzene/ethyl acetate=4), whereby 60 mg (yield: 70%) of a red solid was obtained.

The product was recrystallized from a solvent mixture of benzene-ether-hexane to obtain a sample for analysis.

Mp: 187°–188.5° C., [α]$_D^{20}$+181° C. (c=0.10, dioxane).

NMR(CDCl$_3$)δ(ppm): 2.08(1H, dd, J=15, 4.5 Hz, H$_{8ax}$), 2.21 (3H, s, OCH$_3$), 2.51(1H, dt, J=15, 2 Hz, H$_{8eq}$), 3.00(1H, d, J=19 Hz, H$_{10ax}$), 3.31(1H, dd, J=19, 1.5 Hz, H$_{10eq}$), 3.43(1H, brs, 7-OH), 4.69(1H, s, 9-OH), 5.17 (1H, d, J=18 Hz, H$_{14}$), 5.38(1H, brs, H$_7$), 5.42(1H, d, J=18 Hz, H$_{14}$), 7.76–8.01(2H, m, ArH), 8.24–8.48(2H, m, ArH), 13.19(1H, s, ArOH), 13.52(1H, s, ArOH).

IR(KBr): 3500(NH), 3450(OH), 1745(CO), 1735(CO)cm$^{-1}$.

Ms m/e 426(M+).

Elementary analysis: AsC$_{22}$H$_{18}$O$_9$. Calculated value: C: 61.97, H: 4.26%. Measured value: C: 61.86, H: 4.28%.

EXAMPLE 9

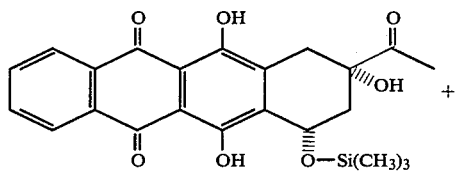

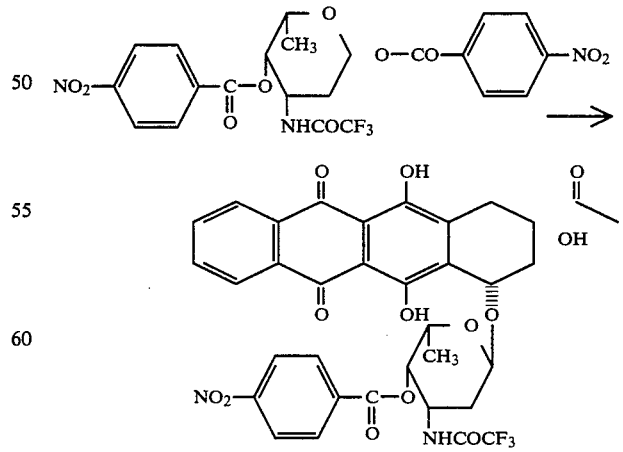

In 15 ml of a solvent mixture of anhydrous methylene chloride-ether (3:1), 48.4 mq (0.11 mmol) of 7-trimethylsilyl-4-demethoxydaunomycinone and 80.0 mg (0.15 mmol) of 2,3,6-trideoxy-1,4-di-O-p-nitrobenzoyl-3-trifluoroacetamido-α-L-lyxohexopyranose were dissolved, and the reaction solution was cooled to −3° C. Then, 0.2 ml (0.02 mmol) of a methylene chloride solution of 0.1M trimethylsilyl trifluoromethanesulfonate was added thereto, and the mixture was stirred for 45 minutes. The reaction solution was poured at 0° C. into a mixture comprising 50 ml of a saturated sodium hydrogen carbonate solution and 50 ml of ethyl acetate and vigorously stirred. Then, the organic layer was separated, washed with a saturated aqueous sodium chloride solution (30 ml) and then dried over anhydrous magnesium sulfate. Then, the solvent was distilled off, whereby 61.2 mg (75%) of glycoside was obtained. The spectrum data of the product were the same as those of Example 5.

EXAMPLE 10

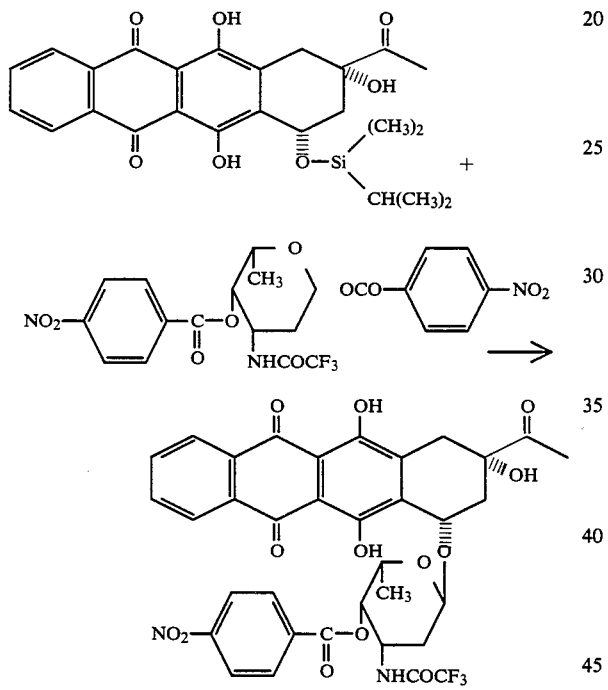

In 15 ml of a solvent mixture of anhydrous methylene chloride-ether (3:1), 48.0 mg (0.11 mmol) of 7-dimethylisopropylsilyl-4-demethoxydaunomycinone and 80.0 mg (0.15 mmol) of 2,3,6-trideoxy-1,4-di-O-p-nitrobenzoyl-3-trifluoroacetamido-α-L-lyxohexopyranose were dissolved, and 0.2 ml (0.02 mmol) of a 0.1M methylene chloride solution of trimethylsilyl trifluoromethanesulfonate was added at −3° C. The mixture was reacted for 1 hour. The reaction mixture was treated in the same manner as in Example 9, whereby glycoside was obtained. The yield was 58.8 mg (72%).

Mp: 166°–170° C.

EXAMPLE 11

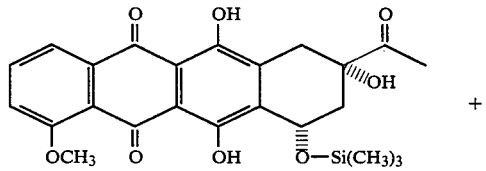

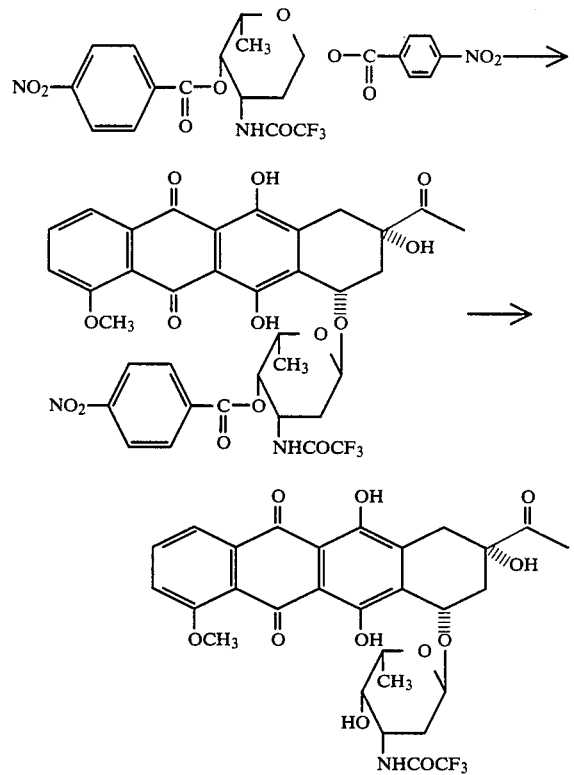

Thirty mg (0.063 mmol) of 7-trimethylsilyl-daunomycinone and 46.0 mg (0.085 mmol) of 2,3,6-trideoxy-1,4-di-O-p-nitrobenzoyl-3-trifluoroacetamido-60 -L-lyxohexopyranose were dissolved in 10 ml of a solvent mixture of anhydrous methylene chloride-ether (3:1), and the reaction solution was cooled to −3° C. Then, 0.15 ml (0.015 mmol) of a 0.1M methylene chloride solution of trimethylsilyl trifluoromethanesulfonate was added thereto, and the mixture was reacted for 1 hour. The reaction solution was treated in the same manner as in Example 9, and purified by silica gel column chromatography, whereby 37.4 mg (yield: 77%) of glycoside was obtained. This product was hydrolyzed in methanol with 0.1N NaOH and quantitatively converted to N-trifluoroacetyldaunomycin.

Mp: 169°–171° C., $[\alpha]_D^{23} = +210°$ (c=0.10 dioxane).

COMPARATIVE EXAMPLE 1

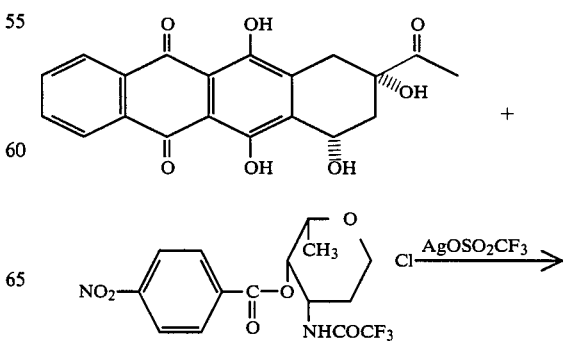

19
-continued

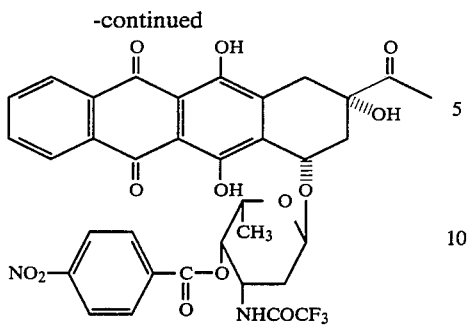

In 4 ml of anhydrous THF, 20.9 mg (0.057 mmol) of 4-demethoxydaunomycinone and 26.7 mg (0.075 mmol) of 1-chloro-N-trifluoroacetyl-O-p-nitrobenzoyl-daunosamine [obtained by treating 2,3,6-trideoxy-1,4-di-O-p-nitrobenzoyl-3-trifluoroacetamido-α-L-lyxohex-opyranose with hydrogen chloride] were dissolved, and 1 ml of an anhydrous ether solution containing 22.0 mg (0.086 mmol) of silver trifluoromethanesulfonate was added thereto under stirring. While shutting out light, the reaction solution was stirred at room temperature for 1 hour, and then diluted with 20 ml of ethyl acetate. The reaction solution was washed with an excess amount of a saturated sodium hydrogen carbonate solution. The organic layer was separated, dried and filtered through cerite, and then the solvent was distilled off, whereby a mixture of 4'-O-p-nitrobenzoyl-3'-N-trifluoroacetyl-4-demethoxydaunomycin and 4-demethoxydaunomycinone in a ratio of about 1:1 was obtained. Without separating the 4'-O-p-nitrobenzoyl-3'-N-trifluoroacetyl-4-demethoxydaunomycin, the reaction residue was dissolved in a small amount of methylene chloride, and 20 ml of methanol was added thereto. The mixture was treated with 0.5 ml of a 0.1N NaOH solution under cooling with ice, neutralized with glacial acetic acid, and then extracted with ethyl acetate. The extracted solution was washed with water, dried and then purified by silica gel column chromatography (benzene/ethyl acetate=4). 9.8 mg (47%) of unreacted 4-demethoxydaunomycinone was recovered, and 16.5 mg (51%) of N-trifluoroacetyl-4-demethoxydaunomycin was obtained.

COMPARATIVE EXAMPLE 2

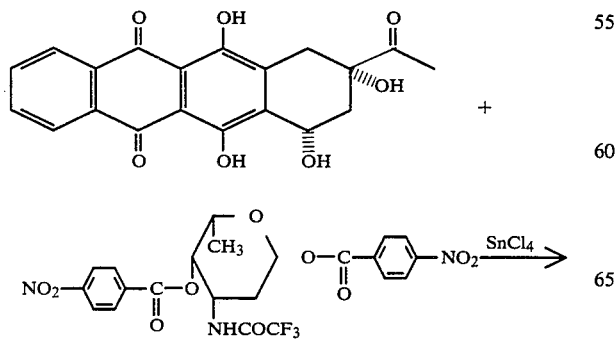

20
-continued

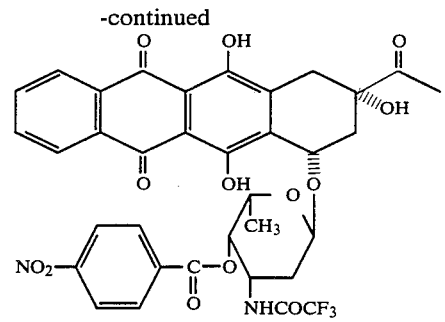

10.3 mg (0.028 mmol) of 4-demethoxydaunomycinone and 20.0 mg (0.037 mmol) of 2,3,6-trideoxy-1,4-di-O-p-nitrobenzoyl-3-trifluoroacetamido-α-L-lyxohex-opyranose were dissolved in 3 ml of anhydrous methylene chloride and 0.5 ml of ether, and about 20 mg (0.08 mmol) of anhydrous tin tetrachloride was added. The mixture was stirred at room temperature for 1 hour. (The yield of the product did not improve even when the reaction was conducted for 3 hours.) The reaction solution was poured into a mixture of a saturated sodium hydrogen carbonate solution and ethyl acetate, whereby the resulting emulsion was washed several times with a saturated aqueous sodium chloride solution and dried, and then the solvent was distilled off. The residual TLC showed the presence of about 50% of glycoside and the starting material aglycone. The product was hydrolyzed with 0.1N NaOH without separating the formed glycoside, and then separated by column chromatography, whereby 8.8 mg (56%) of N-trifluoroacetyl-4-demethoxydaunomycin was obtained.

We claim:

1. In a process for producing an anthracycline derivative, the improvement comprising:
reacting an anthracyclinone derivative of the formula:

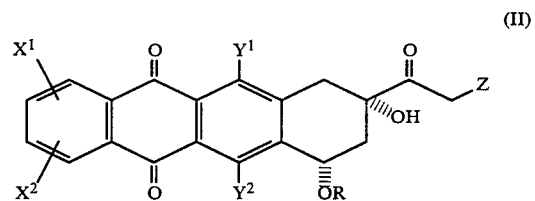

(II)

where R is a hydrogen or a lower trialkylsilyl group, and each of $X^1$ and $X^2$ is a hydrogen atom, a methoxy, a hydroxyl, a halogen, or a lower alkyl; each of $Y^1$ and $Y^2$ is a hydrogen, a lower alkoxy or a hydroxyl; and Z is a hydrogen or a protected hydroxyl; with a 1-acyl-sugar derivative of the formula:

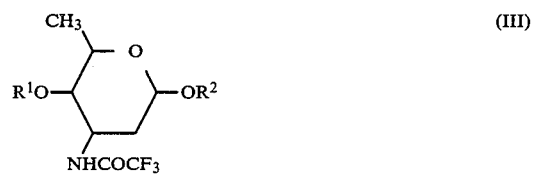

(III)

where each of $R^1$ and $R^2$ are independently a p-nitrobenzoyl, a trifluoroacetyl, and acetyl or a benzoyl; in the presence of a silyl sulfonic acid of the formula:

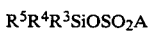

where each of $R^3$, $R^4$ and $R^5$ is a lower alkyl; A is benzenne, toluene, a polyfluoroalkyl or a hydrogen; to obtain an anthracycline derivative of the formula:

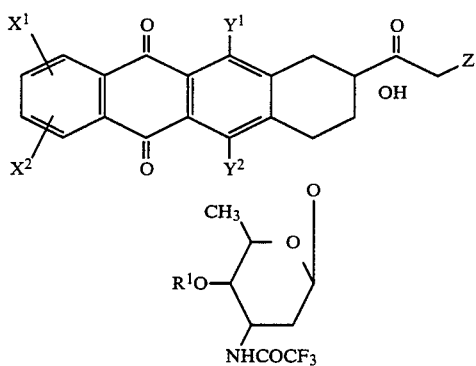

wherein $X^1$, $X^2$, $Y^1$, $Y^2$, Z and $R^1$ are as defined above.

2. The process according to claim 1, wherein the protected hydroxyl group as Z is an acyloxy group, an alkoxy group or a trialkylsilyloxy group, or represents, together with the adjacent carbonyl group, a protective group of the formula:

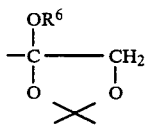

where $R^6$ is a lower alkyl group, or, together further with the 9-hydroxyl group, a protective group of the formula:

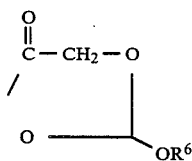

where $R^6$ is as defined above.

3. The process according to claim 1, wherein the silyl sulfonic acid derivative of the formula IV is trimethylsilyl trifluoromethanesulfonate, trimethylsilyl difluoromethanesulfonate, trimethylsilyl chlorodifluoromethanesulfonate, trimethylsilyl 1,1,2,2-tetrafluoroethanesulfonate, triethylsilyl trifluoromethanesulfonate, dimethylisopropylsilyl trifluoromethanesulfonate, t-butyldimethylsilyl trifluoromethanesulfonate, trimethylsilyl perfluorobutanesulfonate, trimethylsilyl perfluorooctanesulfonate, trimethylsilyl methanesulfonate, trimethylsilyl ethanesulfonate, trimethylsilyl benzenesulfonate, trimethylsilyl p-bromobenzenesulfonate or trimethylsilyl p-toluenesulfonate.

4. The process according to claim 1, wherein the silyl sulfonic acid derivative of the formula IV is used in an amount of from 0.1 to 4 equivalents relative to 1 equivalent of the anthracyclinone of the formula II where R is a hydrogen atom, or from 0.05 to 0.3 equivalent relative to 1 equivalent of the anthracyclinone of the formula II where R is a trialkylsilyl group.

5. The process according to claim 1, wherein the reaction is conducted in a solvent mixture comprising a halogen-type solvent selected from the group consisting of methylene chloride and 1,2-dichloroethane, and an ether-type solvent selected from the group consisting of diethyl ether and dimethoxyethane.

6. The process according to claim 1, wherein the reaction is conducted at a temperature of from $-20°$ to $20°$ C.

7. An anthracyclinone derivative represented by the general formula:

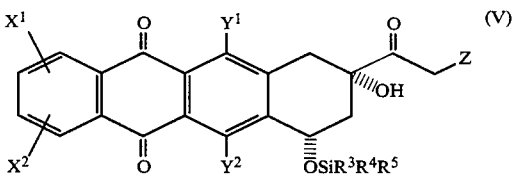

where each of $R^3$, $R^4$ and $R^5$ is a lower alkyl group, each of $X^1$ and $X^2$ is a hydrogen atom, a methoxy group, a hydroxyl group, a halogen atom or a lower alkyl group, each of $Y^1$ and $Y^2$ is a hydrogen atom, a lower alkoxy group or a hydroxyl group, and Z is a hydrogen atom or a protected hydroxyl group.

8. The anthracyclinone derivative according to claim 7, which is represented by the general formula:

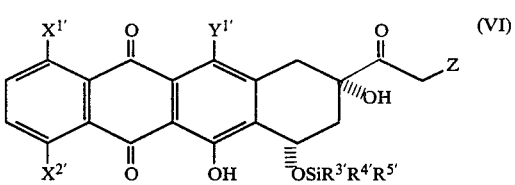

where each of $R^{3'}$, $R^{4'}$ and $R^{5'}$ is a lower alkyl group, each of $X^{1'}$ and $X^{2'}$ is a hydrogen atom, a hydroxyl group or a methoxy group, $Y^{1'}$ is a hydrogen atom or a hydroxyl group, and Z is a hydrogen atom or a protected hydroxyl group.

* * * * *